(12) United States Patent
Powell et al.

(10) Patent No.: US 11,348,232 B2
(45) Date of Patent: May 31, 2022

(54) SYSTEMS AND METHODS FOR DETERMINING PATIENT COMPLIANCE WITH AN ORTHODONTIC DEVICE

(71) Applicants: Stephen Powell, Terre Haute, IN (US); Joseph T. Acklin, Carmel, IN (US)

(72) Inventors: Stephen Powell, Terre Haute, IN (US); Joseph T. Acklin, Carmel, IN (US)

(*) Notice: Subject to any disclaimer, the term of this patent is extended or adjusted under 35 U.S.C. 154(b) by 182 days.

(21) Appl. No.: 16/712,905

(22) Filed: Dec. 12, 2019

(65) Prior Publication Data

US 2020/0193593 A1 Jun. 18, 2020

Related U.S. Application Data

(60) Provisional application No. 62/779,228, filed on Dec. 13, 2018.

(51) Int. Cl.
| | |
|---|---|
| *G06K 9/00* | (2022.01) |
| *G06T 7/00* | (2017.01) |
| *G16H 20/00* | (2018.01) |
| *G16H 10/60* | (2018.01) |
| *G01N 21/64* | (2006.01) |
| *A61C 7/36* | (2006.01) |
| *A61C 7/08* | (2006.01) |

(52) U.S. Cl.
CPC ........ *G06T 7/0012* (2013.01); *G06K 9/00221* (2013.01); *G16H 10/60* (2018.01); *G16H 20/00* (2018.01); *A61C 7/08* (2013.01); *A61C 7/36* (2013.01); *G01N 2021/646* (2013.01); *G06K 2209/057* (2013.01); *G06T 2207/10016* (2013.01); *G06T 2207/30036* (2013.01)

(58) Field of Classification Search
CPC ........................................... G06T 2207/30036
See application file for complete search history.

(56) References Cited

U.S. PATENT DOCUMENTS

| | | | |
|---|---|---|---|
| 10,001,771 B2 | 6/2018 | Matty | |
| 11,024,431 B2 * | 6/2021 | Stone-Collonge | ... A61B 5/0077 |
| 2008/0294405 A1 | 11/2008 | Kitching et al. | |

(Continued)

OTHER PUBLICATIONS

Roisin, Brezulier, & Sorel. Remotely-controlled orthodontics: fundamentals and description of the Dental Monitoring system, J Dentofacial Anom Orthod 2016;19:408.

(Continued)

*Primary Examiner* — Oneal R Mistry
(74) *Attorney, Agent, or Firm* — Bruce J. Bowman (57) ABSTRACT

A system is disclosed for remotely determining patient compliance with an orthodontic device. This system includes a handheld portable computing device having a camera, and the handheld portable computing device is configured for communication via the Internet. A patient compliance application is executed by the handheld portable computing device, and an image analysis module is associated with the patient compliance application. The image analysis module receives an image from the camera, and the image analysis module analyzes the image to determine a presence status of the removable orthodontic device. The patient compliance application is further configured to communicate the presence status to an orthodontic provider at a remote location relative the user.

14 Claims, 6 Drawing Sheets

(56) References Cited

U.S. PATENT DOCUMENTS

| | | | |
|---|---|---|---|
| 2017/0056131 A1* | 3/2017 | Alauddin | A61B 5/0022 |
| 2017/0304021 A1 | 10/2017 | Nobrega et al. | |
| 2018/0000563 A1 | 1/2018 | Shanjani et al. | |
| 2018/0042698 A1 | 2/2018 | Salah et al. | |
| 2018/0204332 A1 | 7/2018 | Salah et al. | |
| 2018/0206940 A1 | 7/2018 | Salah et al. | |
| 2018/0353263 A1* | 12/2018 | Salah | G06T 7/0012 |
| 2019/0269482 A1* | 9/2019 | Shanjani | A61C 7/002 |
| 2020/0193593 A1* | 6/2020 | Powell | G06K 9/00221 |

OTHER PUBLICATIONS

Rao, Mokhtar, & Iskandar. Managing orthodontic needs through mobile apps, Journal of Hospital Management and Health Policy, Mar. 2018.

Sellke. Remote monitoring of treatment-less time, more control, Doctalk Dental—Orthodontic Practice, Mar. 20, 2017.

\* cited by examiner

FIG. 5

SYSTEMS AND METHODS FOR DETERMINING PATIENT COMPLIANCE WITH AN ORTHODONTIC DEVICE

CROSS REFERENCE TO RELATED APPLICATIONS

The present application claims the benefit of U.S. Provisional Patent Application No. 62/779,228, filed Dec. 13, 2018, the entirety of which is incorporated herein by reference.

BACKGROUND

The technical field generally relates to orthodontics. More specifically, the technical field of the present application relates generally to determining patient compliance with orthodontic devices.

Orthodontic devices are frequently utilized to straighten teeth and to correct issues with "bite." Many orthodontic devices include components that are removable (e.g. retainers, teeth straightening trays, elastics, and aligners). For the orthodontic device to perform correctly, these removable components must be worn by the user. Failure to wear these components as directed can increase the length of treatment as well as the number of orthodontic office visits required during the treatment.

Orthodontists are presently only able to determine patient compliance when the patient is within their office. They are not able to determine if a patient is correctly wearing the orthodontic device outside of the office. Mobile applications are presently constrained to sending reminder notifications, such as reminding a patient to please wear their elastics.

Many orthodontists perform their services based on a fixed fee agreement (e.g. independent the length of treatment), and can lose money due to patient non-compliance. Therefore, further technological developments are desirable in this area.

SUMMARY

One form of the present application includes a system for determining patient compliance with an orthodontic device. Other embodiments include unique apparatuses, systems, and methods for determining patient compliance with orthodontic devices. In one specific non-limiting embodiment, the present application utilizes an application ("app") on a smartphone to determine if a patient is wearing an orthodontic device (e.g. elastics, commonly known as "rubber bands", a retainer, a straightening tray, or the like). Further embodiments, inventions, forms, objects, features, advantages, aspects, and benefits of the present application are otherwise set forth or become apparent from the description and drawings included herein.

BRIEF DESCRIPTION OF THE DRAWINGS

The description herein makes reference to the accompanying drawings wherein like reference numerals refer to like parts throughout the several views, and wherein.

DETAILED DESCRIPTION

For purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated device, and any further applications of the principles of the invention as illustrated therein being contemplated as would normally occur to one skilled in the art to which the invention relates.

As utilized herein, the term "removable orthodontic device" includes any orthodontic device in which all of the orthodontic device, or a portion and/or subcomponent of the orthodontic device, can be removed and/or installed by a user. Although a variety of removable orthodontic devices are contemplated herein, exemplary removable orthodontic devices include elastics (e.g. "rubber bands"), teeth straightening trays, teeth whitening trays, aligners, retainers, or any other removable orthodontic device as would be understood to a person of ordinary skill in the art ("POSITA").

Figure 1A:
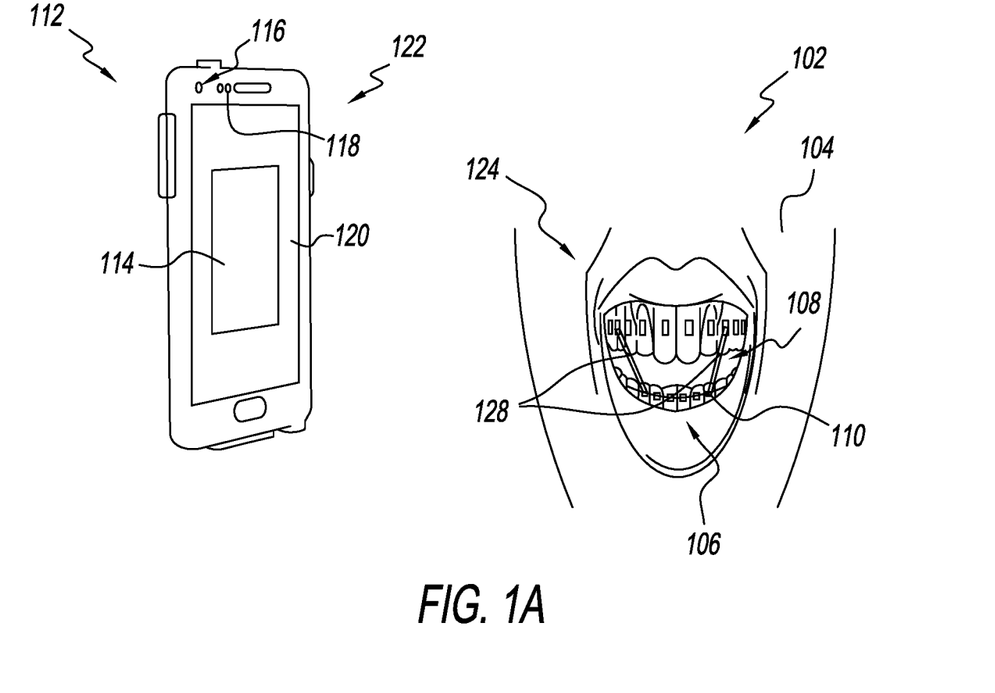
FIG. 1A is an illustration of an orthodontic compliance check performed on a user wearing elastics, according to one form of the present application.

FIG. 1A depicts one form of a patient compliance check performed by a handheld portable computing device. A patient 102 is illustrated as having an orthodontic device 106 within an oral cavity 124. The orthodontic device 106 is depicted as including a removable orthodontic device/removable orthodontic component 108. As was previously aforementioned, although the removable orthodontic device 108 is depicted as elastics 128, a variety of removable orthodontic devices 108 are contemplated herein. Additionally, as would be understood by a POSITA, although the elastics 128 are depicted as being worn in a specific manner, the elastics 128 mounting locations, number of elastics 128 present, strength of the elastics 128, etc. will depend upon the specific orthodontic treatment prescribed to the patient 102.

A handheld portable computing device is depicted at 112. This handheld portable computing device 112 includes a camera 116. The handheld portable computing device 112 includes memory, processing, and communication hardware which are configured to execute a variety of programs and applications. The handheld portable computing device 112 is depicted as smartphone 112; however, a variety of handheld portable computing devices 112 are contemplated herein, including tablets, laptops, portable console games, and the like.

The handheld portable computing device 112 includes a display screen 120, which in some forms can additionally receive various user inputs. In one form, the camera 116 is a forward facing camera 116 located on the front face 122 of the handheld portable computing device 112. However, it is also contemplated that the camera 116 can be integrated with the handheld portable computing device 112 at a variety of locations, as is known (e.g. the camera 116 can be front facing, rear facing, and/or one or multiple cameras integrated with the handheld portable computing device 112).

The handheld portable computing device 112 can be configured to communicate via the Internet (e.g. wirelessly through a cellular wireless network, through a hardwired connection, or through a wireless area network). Although wireless communication is utilized in a preferred form, wired communication can be employed.

Figure 1B:
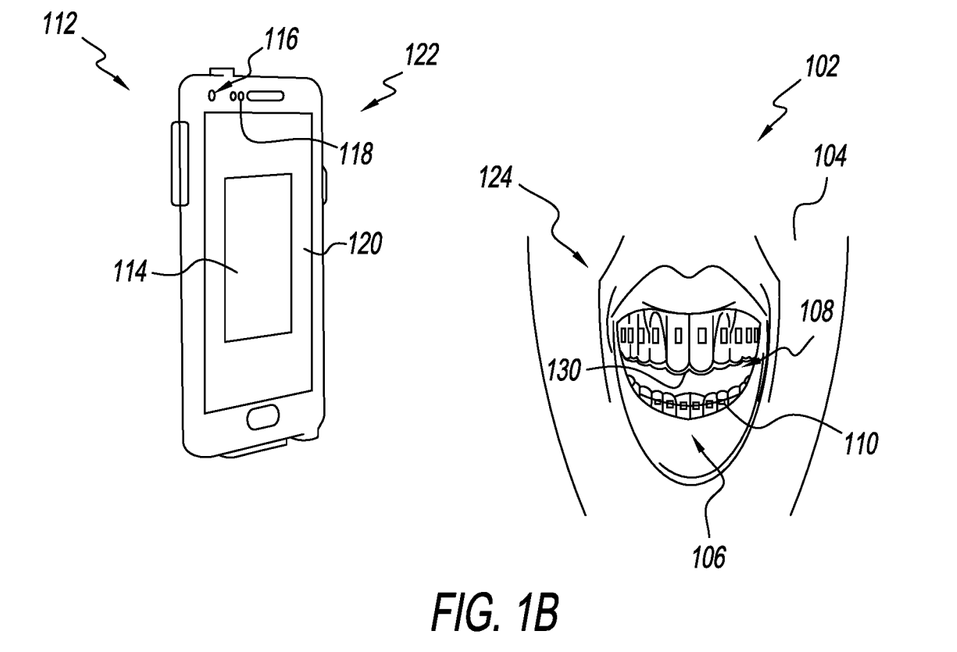
FIG. 1B is an illustration of an orthodontic compliance check performed on a user wearing a clear aligner tray, according to a further form of the present application.

Referring now to FIG. 1B, a patient 102 is illustrated as having an orthodontic device 106 within an oral cavity 124. This removable orthodontic device 108 is depicted as a clear aligner tray 130. However, as was previously described, a variety of removable orthodontic devices 108 are contemplated herein. As is illustrated, the removable orthodontic device 108 can include a photoluminescent material, depicted at 110. In this form, the handheld portable computing device 112 includes a UV emitting light 118.

Referring now to FIGS. 1A and 1B, a patient orthodontic compliance application 114 is depicted as being displayed on the display screen 120 of the handheld portable computing device 112. This patient orthodontic compliance application 114 is configured to determine if a patient 102 is in compliance with a specific orthodontic treatment by making a determination as to whether the patient is wearing the removable orthodontic device 108. In a variety of forms, the orthodontic compliance application 114 may be a single application or can include a variety of distributed applications, and the functions of the application (as will be discussed hereinafter) may be performed by hardware or software.

Figure 2:
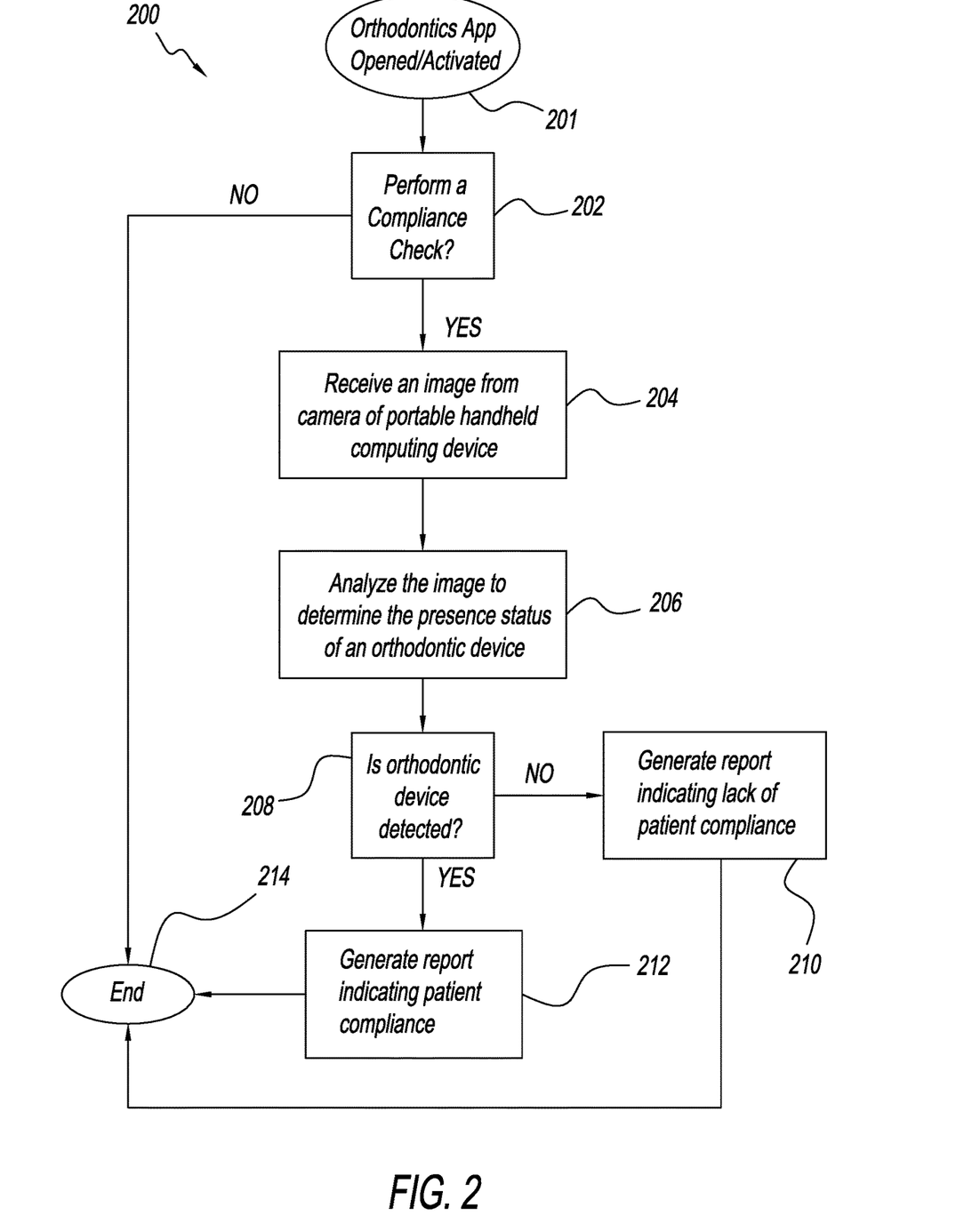
FIG. 2 depicts a schematic flow diagram of an exemplary method for performing an orthodontic compliance check.

Referring now to FIG. 2, one embodiment of the operation 200 of the orthodontic compliance application 114 will now be discussed. The orthodontics application (app) is opened/activated 201 by the patient. At decision block 202, the orthodontic compliance application 114 determines whether to perform a compliance check.

In various forms, the orthodontic compliance application 114 can automatically determine to perform a compliance check and/or the compliance check can be performed in response to a manual input by the patient 102, who is the user of the application 114. For example, the user 102 may select a prompt within the application 114 to begin a compliance check. Alternatively, upon the user opening the application 114 a compliance check may begin. In further forms, the compliance application 114 can begin a compliance check automatically through a time or date based schedule and/or the compliance application 114 can communicate with other applications and processes within the handheld portable computing device 112, such that a user initiated action, distinct from the compliance application 114, can initiate a compliance check (e.g. when the user 102 unlocks the handheld portable computing device 112). In a further form, the compliance check can automatically begin when the mouth 104 of the user 102 is in the field of view of the camera 116.

When a compliance check is to begin, the application 114 can provide a variety of prompts to the user 112. For example, the application 114 can prompt the user 112 to open their mouth 104. Additionally, the application 114 can aid the user in directing the camera 116 toward the mouth 104 such that an image captured by the camera 116 will include a portion of the orthodontic device 106. This can be done by the application 114 providing instructions to the user 102 such as "turn camera slightly to the left", "please pull your lips away from your gums", and "please open your mouth wider." As will be understood to a POSITA, the portion of the orthodontic device 106 which should be included in the image will depend upon the type of removable orthodontic device 108 for which compliance is being determined (e.g. In the case of elastics 128, the elastics 128 should be captured by the camera 116 in the image. Alternatively, in the case of a teeth straightening tray 108, it may only be necessary for the front portion of the tray 108 to be captured by the camera 116 in the image).

At step 204, the application 114 receives the image from the camera 116. As utilized herein, the term image can include a still image, a series of still images, and video (delayed, "real-time", or the like). As will be discussed hereinafter, this image can then be processed to determine the presence status of the removable orthodontic device 108. As utilized herein, the term presence status refers to the status of the removable orthodontic device 108, specifically if the removable orthodontic device 108 is present or absent from the oral cavity 124 of the user 102.

In one form, a pattern recognition algorithm can be utilized to detect the presence status of the removable orthodontic device 108 (e.g. a "positive" or "present" presence status indicates that the removable orthodontic device 108 is present within the mouth of the user). In this form, it is contemplated that a variety of facial recognition algorithms, in addition to line detection algorithms, can be utilized to distinguish between the face of the user 102, the features present within the mouth 104 of the user 102 (e.g. teeth, gums, tongue, etc.), and the removable orthodontic device 108. In one specific form, the algorithm can detect the shape of anchors, such as those which may be utilized with teeth straightening trays 108 in FIG. 1B, to determine the presence of the teeth straightening tray 108. It has been discovered that line detection algorithms are well suited to determining the presence status of elastics 128 within the oral cavity 124 of the user 102, as are illustrated in FIG. 1A.

In a further form, a glare detection algorithm can be utilized to detect the presence status of the removable orthodontic device 108. In this form, the algorithm compares the various "glares" in the image to determine if the removable orthodontic device 108 is present. As would be understood by a POSITA, this form can be especially useful when dealing with clear polymeric materials (presently most teeth straightening trays, aligners 130, and retainers are manufactured from such a clear polymeric material). In this manner, the algorithm can detect the differences between the plastic removable orthodontic device 108 and teeth, gums, etc. to determine if the removable orthodontic device 108 is present.

In yet a further form, a photoluminescent detection algorithm can be utilized to detect the presence of photoluminescent material 110 within the oral cavity 124 of the user 104. For example, where photoluminescent material 110 is present within the removable orthodontic device 108, as illustrated in FIG. 1B, the application 114 can activate the UV emitting light 118 while the camera 116 is taking the image. A photoluminescent detection algorithm can then be utilized to detect the presence of photoluminescent material 110 within the oral cavity 124 (e.g. via a reflection or glare algorithm). The presence, or absence, of photoluminescent material 110 can be utilized to determine the presence status of the removable orthodontic device 108 within the oral cavity 124 of the user 102. Specifically, if the application 114 determines photoluminescent material 110 is present, a "present" status should be assigned to the removable orthodontic device 108.

Although a variety of image processing techniques have heretofore been described separately, it is to be understood that any one, or any combination, of these techniques can be utilized to determine the presence of the removable orthodontic device 108 within the mouth 104 of the user 104. Additionally, it is contemplated that a variety of additional image processing techniques can be utilized to detect the presence status (the presence or absence) of the removable orthodontic device 108. Moreover, it is contemplated that this image analysis can be performed in substantially real-time, or can be performed with a time delay.

In various forms, image analysis can be performed by the compliance application 114, by a separate application on the handheld portable computing device 112, or by a separate application on a server or database which is in communication with the handheld portable computing device 112. In one form, an image analysis module can perform the image processing, and the image analysis module (not shown) is associated with the compliance application 112. In one form, the image analysis module can be integral to the compliance application 114. However, in further forms, it is contemplated that the image analysis module can be a separate application on the handheld portable computing device 112, or can be located on a separate computing device (e.g. a server in an orthodontist's office).

Referring back to FIG. 2, the compliance application determines if the removable orthodontic device 108 was detected during the image analysis at 208. If the removable orthodontic device 108 was determined to be present within the mouth 104 of the user 102, the application 114 can generate a report indicating that the patient was compliant with their orthodontic treatment during that particular compliance check. If the removable orthodontic device 108 was determined to be absent, the application 114 can generate a report indicating that the patient is not in compliance with their orthodontic treatment.

In further forms, the compliance data from a plurality of compliance checks can be tabulated as patient compliance data to determine, for example, how frequently the patient wears their removable orthodontic device 108. This can be depicted, for example, as a total number of compliance checks performed and how many of those checks indicated compliance. In a further form, the compliance data can include a date and time stamp with the indication of compliance or lack of compliance. In one form, the frequency of the compliance checks can be determined in part based on this patient compliance data. For example, if several compliance check have indicated positive compliance, future checks may be performed less frequently. On the other hand, one or more indications of lack of compliance may lead to more frequent compliance checks.

It is contemplated that the compliance application 114 can communicate these compliance reports and/or compliance data to a variety of third parties, including parents, orthodontists, device manufacturers, or the like. Additionally, the application 114 can communicate and/or receive various data from a variety of sources. For example, an orthodontist may directly communicate a variety of data to a patient through the application 114 and/or the patient 102 may be able to communicate to the orthodontist. In a further form, the application 114 can transmit a photograph of the oral cavity 124 of the user to the orthodontist, in addition to the compliance data.

In one form, the compliance application 114 includes and/or communicates with mobile device management ("MDM") software. As would be understood by a POSITA, a variety of MDM software presently exists for a variety of software platforms such as Apple, Android, and Windows. In this form, upon determining a lack of compliance (e.g. the application 114 performed a compliance check in which removable orthodontic device 108 was not present) the compliance application 114 can restrict and/or "lock-out" the patient 102 from other predetermined applications. For example, a parent of the patient 102 may have permission to access the MDM software via application 114. The parent may input that the patient 102 should not have access to a variety of game applications, shopping applications, and/or other applications should the application 114 determine a lack of compliance. As would be readily understood, this application restriction can serve as an incentive for a patient 102 to comply in wearing their removable orthodontic device 108.

In yet a further form, the cost of orthodontic treatment for the patient 102 is affected by the compliance data generated by the application 114. For example, an orthodontist may determine that if a specified number of compliance checks return the result of "non-compliant", the cost of treatment for the patient 102 may increase. On the other hand, an orthodontist could determine that a price discount would be given should a patient 102 have a certain number of consecutive compliance checks which indicate "compliance". As would be understood to a POSITA, a variety of financial incentives/disincentives can be attached to the indications of "compliance" or "non-compliance" by the application 114. In structuring fees based upon patient compliance in wearing their removable orthodontic device 108, an orthodontist can reduce the likelihood that they will lose money due to lengthened treatment schedules resulting from a lack of patient compliance.

One non-limiting example of use of the device for performing a simple "bands check" will now be discussed. A compliance application 114 has been downloaded to the smartphone 112 of a user 102. The compliance application 114 determines "It is 1 p.m., it is time to perform a bands check". The compliance application 114 prompts the user 102 of the bands check. This can be done via a pop-up on the screen 120 of the smartphone 112. The user 102 will now hold the smartphone 112 with the camera 116 facing toward their open oral cavity 124. The application 114 may prompt the user to "please direct the phone leftward such that your rubber bands appear on the image displayed on your screen."

In some forms, the application 114 can utilize facial feature recognition technology, as would be known to a POSITA, to focus the camera 116 onto the oral cavity 124 of the user 102. It is also contemplated that the application 114 can utilize this facial feature recognition technology to confirm the identity of the user 102. Such analysis could prohibit a user 102 from substituting a friend's mouth for their own (e.g. to gain a "present" compliance check).

Once the compliance application 114 has determined that a viable image has been received, the image is analyzed. In one form, this image analysis can occur via a pattern recognition algorithm. This pattern recognition algorithm can be utilized to determine if lines are present within the oral cavity 124 of the user. If one or more lines are detected, the application 114 may indicate "compliance". However, in further forms, the application 114 may further analyze any located lines to determine, e.g. number of lines, slope of the lines, length of lines in relation to determined mouth size, etc. to compare against known line values for a particular user 102 to determine patient compliance. The resulting compliance determination can be shown to the user 102 and may be communicated to orthodontist at a remote location.

Figure 3:
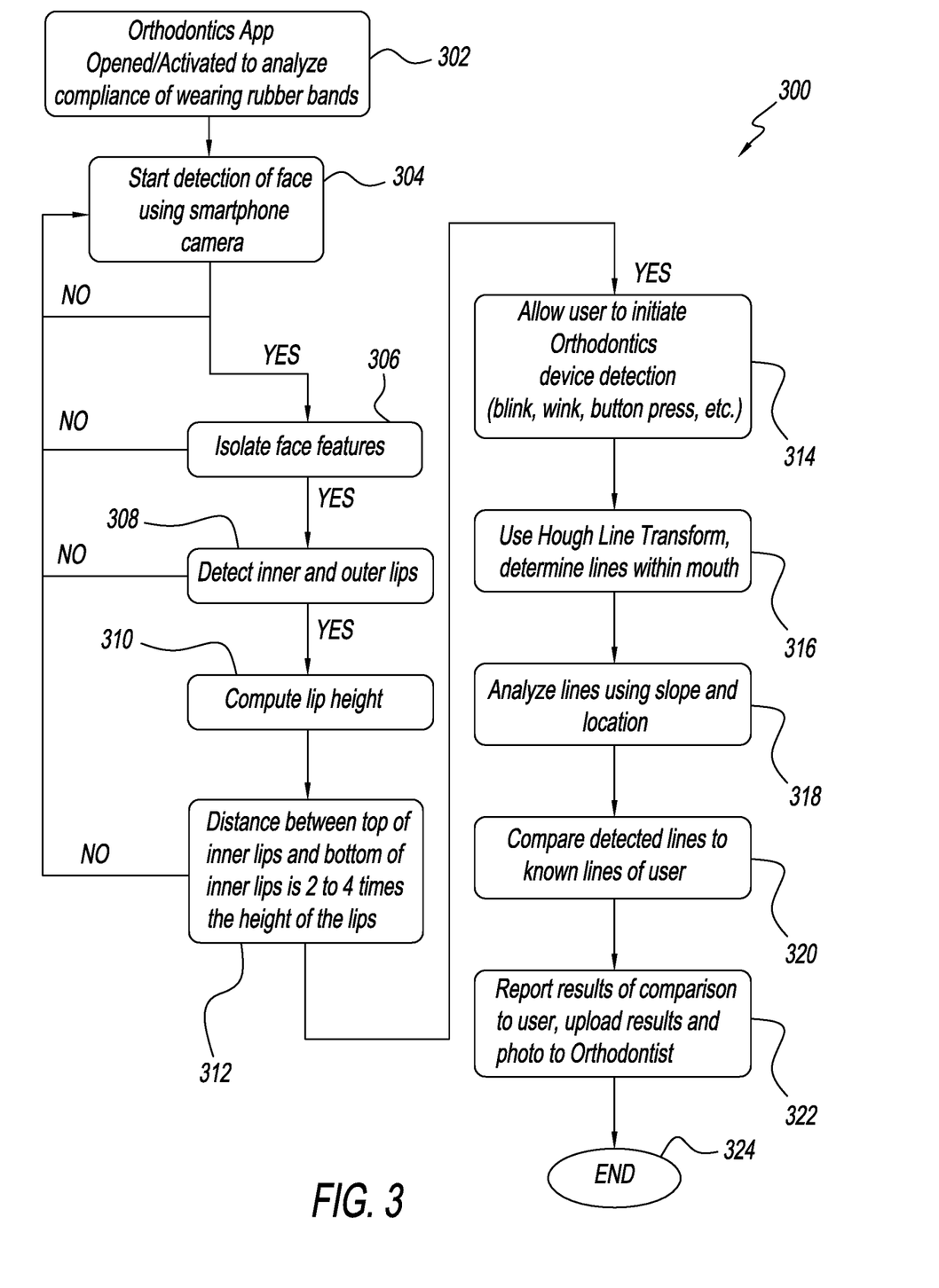
FIG. 3 depicts a schematic flow diagram of an exemplary method for performing an orthodontic compliance check for elastics.

Referring now to FIG. 3, an exemplary elastics check 300 will now be discussed. At 302 a compliance application 114 is opened to analyze patient compliance in wearing elastics 128 (e.g. rubber bands). A decision block 304 determines whether to start detection of the face of a user 102 utilizing the camera 116 of a smartphone 112. In response to a "Yes" determination from decision block 304, the facial features of a user 102 are isolated at 306. The isolation of an oral cavity 124 of the user 102 can be performed utilizing facial feature recognition software.

To determine if the user 102 has an open oral cavity 124, a determination of lip spacing can be utilized. For example, the inner and outer lips of the oral cavity 124 are detected at 308. The lip height is computed at 310. At 312, it is determined if the oral cavity 124 of the user 102 is open. In one form, an "oral cavity open" determination can be made in response to a finding that the distance between the top and inner lips and bottom of the inner lips is two (2) to four (4) times the height of the lips. If the oral cavity 124 of the user 102 is opened, a user 102 can initiate orthodontic device detection at 314. In various forms, the user 102 can initiate the orthodontic device detection through a variety of inputs, which include, but are not limited to, blinking both eyes, winking one eye, or pressing a button displayed on a screen 120 of the smartphone 112.

A pattern recognition algorithm can be utilized to determine if elastics 128 are present within the oral cavity 124. In one form, a Hough Line Transform is utilized at 316 to detect lines present within the oral cavity of a user. These detected lines are analyzed at 318 to determine the slope and location of the lines. At 320, the detected lines and characteristics of the lines (e.g. slope, location, and count) are compared with the known lines of the user 102. In response to a determination that the detected lines are substantially equivalent to known lines, the application determines that elastics 128 are present and a "compliance" presence status is indicated. However, if no lines are detected, or if the lines do not correspond to known lines of the particular user 102, a "non-compliance" presence status will be indicated. At 322, the results of the comparison are reported to the user 102 and an orthodontist. In one form, a photograph of the oral cavity 124 of the user 102 can also be transmitted to the orthodontist. The application ends at 324.

Figure 4:
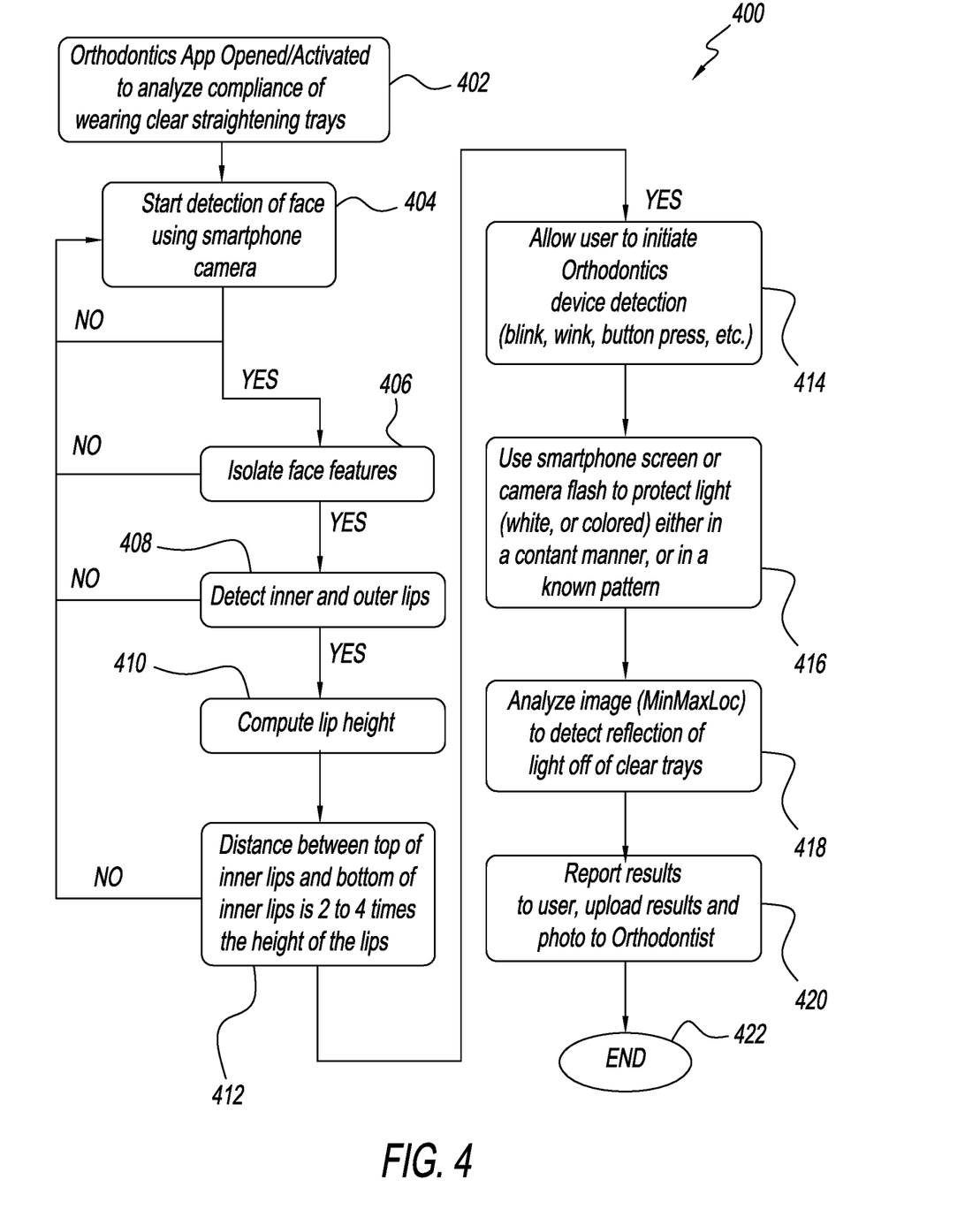
FIG. 4 depicts a schematic flow diagram of a method for performing an orthodontic compliance check for a teeth straightening tray, according to one form of the present application.

FIG. 4 depicts one form of an orthodontic compliance check 400, as can be utilized to determine compliance with a device made of a clear polymeric material, such as an aligner 130, retainer, straightening tray, or the like (e.g. aligner tray 130). At 402 a compliance application 114 is opened to determine patient compliance in wearing clear straightening trays 130. Decision block 404 determines whether to start detection of the face 104 of a user 102 using the camera 116 of a smartphone 112. In response to a "YES" determination, facial features are isolated at 406. As was discussed above with regard to FIG. 3, this isolation of the oral cavity 124 of a user 102 can be performed utilizing facial feature recognition software, as is known in the art.

The inner and outer lips of the oral cavity 124 are detected at 408. The lip height is computed at 410. At 412, it is determined if the oral cavity 124 of the user 102 is opened. In one form, this determination can be made in response to a finding that the distance between the top and inner lips and bottom of the inner lips is two (2) to four (4) times the height of the lips, as was discussed with regard to FIG. 3. If the oral cavity 124 of the user 102 is open, a user 102 can initiate an orthodontic device detection at 414. It is contemplated that the user 102 can initiate the orthodontic device detection through a variety of inputs, which include, but are not limited to, blinking both eyes, winking one eye, or pressing a button displayed on a screen of the smartphone. In further forms, orthodontic device detection can be initiated automatically, e.g. when the open oral cavity 124 of the user 102 is detected by the application 114.

At 416, the smartphone 112 projects lights, patterns, and/or colors into the oral cavity 124 of a user 102. Such projection can be done through a display screen 120 of the smartphone 112, or through one or more led lights 118 as are presently utilized for a smartphone 112 camera 116 "flash". These projections of lights, patterns, and/or colors can be constant, flashing, or the like depending upon the desired reflection to be analyzed. As would be understood to a POSITA, light projecting into the oral cavity 124 of a user 102 will reflect from a removable orthodontic device 108, which are typically constructed of a polymer. However, other features naturally present within the oral cavity 124 of a user 102, such as teeth, gums, etc. will have a significantly reduced reflection relative polymeric materials.

As is illustrated at 418, the application 114 analyzes the image received from the camera 116. In the form depicted with regard to FIG. 4, this analysis determines if the reflection of light is consistent with the expected reflection of the orthodontic device 108 of the user 102. For example, in a MinMaxLoc system, if the reflection detected exceeds a minimum reflective value, a "compliance" presence status can be indicated (e.g. the removable orthodontic device 108 is inserted into the oral cavity 124 of a user 102). On the other hand, if such a reflection detected in the image falls below such minimum reflective value, a "non-compliance" presence status can be indicated (e.g. because the only reflection is from teeth, gums, etc. the application can assume the removable orthodontic device is not located within the oral cavity 124 of the user 102).

At 420, the results of the analysis are reported to the user 102 and an orthodontist. In one form, a photograph of the oral cavity 124 of the user 102 can also be transmitted to the orthodontist. The application ends at 422.

Figure 5:
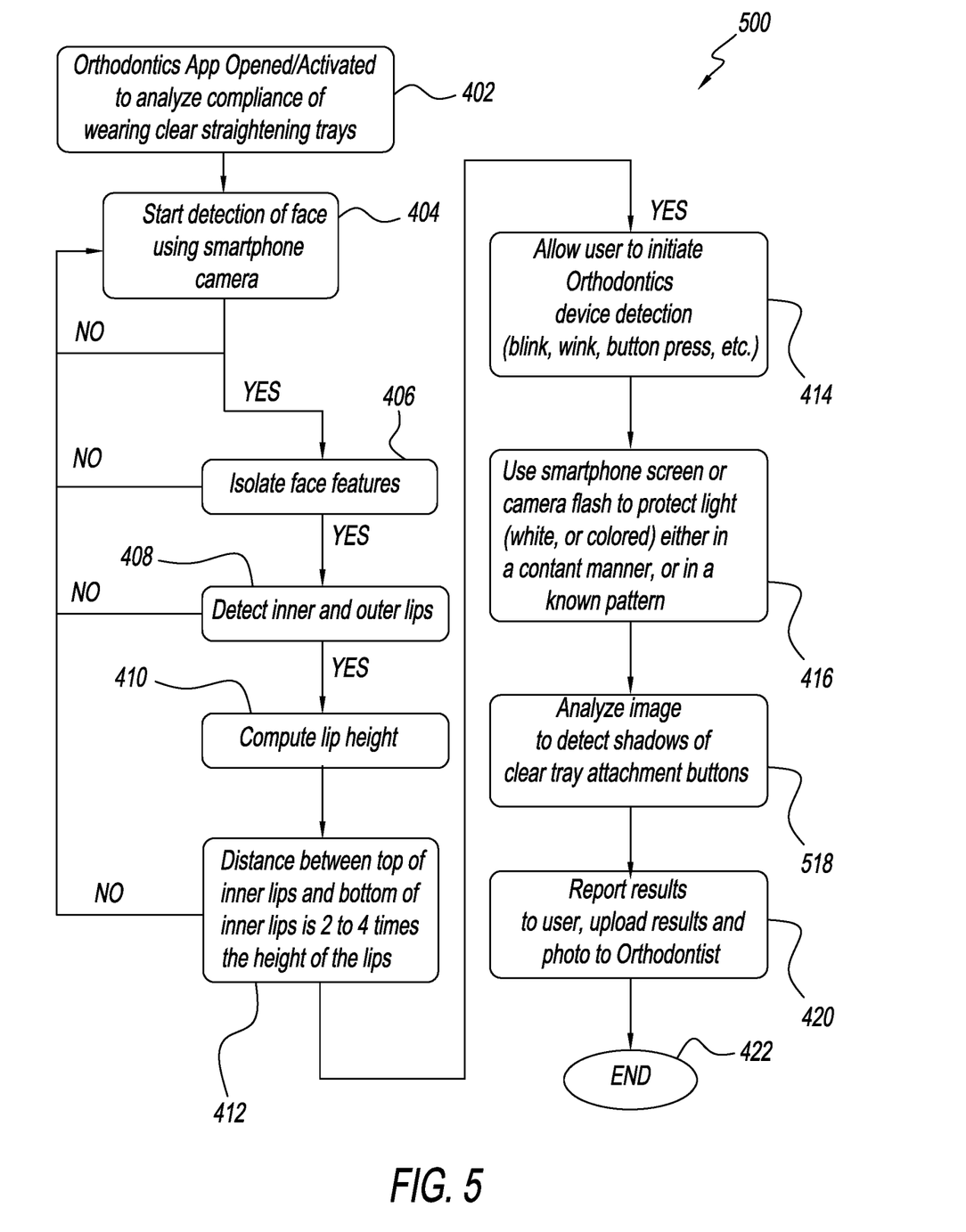
FIG. 5 depicts a schematic flow diagram of a method for performing an orthodontic compliance check for a teeth straightening tray, according to a further form of the present application.

FIG. 5 depicts a further form of an orthodontic compliance check 500, as can be utilized to determine compliance with an aligner tray 130 or whitening tray. The primary difference between orthodontic compliance check 500 and orthodontic compliance check 400 lies in the method of analyzing the image. Rather than utilizing MinMaxLoc as was previously discussed with regard to 418, after the projection of lights, patterns, and/or colors into the oral cavity 124 of a user 102 at 416, compliance check 500, at 518, analyzes the image received from the camera 116 to search for the shadow of a known feature of the orthodontic device 108. In one form, the image is analyzed to detect shadows of clear tray attachment buttons, commonly located on aligners 130.

Should the application 114 detect shadows of clear tray attachment buttons during the image analysis, a "compliance" presence status will be indicated. However, if the application 114 fails to detect the shadows of such attachment buttons, a "non-compliance" presence status will be indicated, demonstrating that the oral cavity 124 of the user 102 fails to include the removable orthodontic device 108. As was previously discussed with regard to FIG. 4, this presence status will then reported to the user and an orthodontist at 420.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A system for remotely determining patient compliance with an orthodontic device, comprising:
   a removable orthodontic device configured for insertion into an oral cavity of a user;
   a handheld portable computing device including a camera, wherein the handheld portable computing device is in electronic communication with the Internet;
   a patient compliance application executed by the handheld portable computing device, wherein an image analysis module is associated with the patient compliance application, wherein the image analysis module receives an image from the camera, the image including at least a portion of the oral cavity of the user, and wherein the image analysis module analyzes the image utilizing at least one of a line recognition algorithm, a pattern recognition algorithm, a glare analysis algorithm, and a photoluminescence analysis, to determine the presence status of the removable orthodontic device; and
   wherein the patient compliance application is further configured to communicate the presence status, via the Internet, to an orthodontic provider at a remote location relative the user.

2. The system of claim 1, wherein the handheld portable computing device further includes a display screen located on a front face of the device, wherein the camera is further located on the front face of the device, wherein at least one of lights, colors, and patterns are displayed on the screen and directed toward the oral cavity of the user.

3. The system of claim 1, wherein the manual input further comprises at least one of winking and blinking, and wherein the image analysis module is configured to begin analysis of the image in response to a manual input of a user.

4. The system of claim 2, wherein the patient compliance application is configured to begin automatically based on at least one of a predetermined time based schedule, a predetermined date schedule, and an unlocking of the handheld portable computing device.

5. A method for determining patient compliance with an orthodontic device, comprising:
   providing a removable orthodontic device, wherein the removable orthodontic device is configured for insertion within an oral cavity of a user;
   providing a handheld portable computing device configured to execute a patient compliance application, wherein the handheld portable computing device is configured to communicate via a wireless network, wherein the handheld portable computing device includes an integral camera, and wherein the patient compliance application is configured to perform a patient compliance check, the patient compliance check, comprising:
   isolating the oral cavity of the user via a facial feature recognition analysis;
   receiving an image from the camera, wherein at least a portion of the oral cavity of the user is included in the image;
   analyzing the image to determine a presence status of the removable orthodontic device;
   processing the image via at least one of a line recognition algorithm, a pattern recognition algorithm, a glare analysis algorithm, and a photoluminescence analysis; and
   communicating the presence status to an orthodontic provider via the wireless network.

6. The method of claim 5, further comprising emitting at least one of lights, colors, and patterns from a screen of the handheld portable computing device, and analyzing a reflection of the at least one of lights, colors, and patterns, to determine the presence status of the removable orthodontic device, and wherein the handheld portable computing device is selected from the group of handheld portable computing devices consisting of a smartphone, a tablet, and a game system.

7. The method of claim 5, wherein analyzing the image further comprises performing a Hough Line Transform to determine a presence status of elastics within the oral cavity of a user.

8. The method of claim 5, wherein the patient compliance application is configured to perform the compliance check in response to one of a predetermined time based schedule, a predetermined date schedule, and an unlocking of the handheld portable computing device.

9. A system, comprising:
   a removable orthodontic device configured for insertion into an oral cavity of a user;
   a patient compliance application executed on a handheld portable computing device, wherein the handheld portable computing device is associated with the user, wherein the handheld portable computing device includes an integral camera, wherein an image analysis module is associated with the patient compliance application, and wherein the image analysis module receives an image from the camera; and
   wherein the image analysis module processes the image utilizing at least one of a line recognition algorithm, a pattern recognition algorithm, a glare analysis algorithm, and a photoluminescence analysis, to determine a presence status of the removable orthodontic device within the oral cavity of the user.

10. The system of claim 9, wherein the image analysis module utilizes a facial feature recognition analysis to isolate the oral cavity of the user, and wherein the patient compliance application is further configured to communicate the presence status, via the Internet, to an orthodontic provider at a remote location relative the user.

11. The system of claim 10, wherein the image further comprises at least one of a still image, a series of still images, a delayed video, and a "real-time" video, and wherein the removable orthodontic device further comprises at least one of an elastic, a straightening tray, an aligner, and a retainer.

12. The system of claim 11, wherein the handheld portable computing device further comprises one of a smartphone, a tablet, a portable gaming system, and a laptop.

13. The system of claim 11, wherein the handheld portable computing device includes a screen, wherein at least one of lights, colors, and patterns are displayed on the screen and are directed toward the oral cavity of the user to be reflected from the removable orthodontic device.

14. The system of claim 10, wherein the patient compliance application is configured utilize the facial feature recognition analysis to confirm an identity of the user.

* * * * *